United States Patent

Buendia et al.

[11] Patent Number: 4,601,854
[45] Date of Patent: Jul. 22, 1986

[54] PROCESS FOR THE PRODUCTION OF PREDNISONE 17.21-DIACYLATES

[75] Inventors: Jean Buendia, Le Perreux sur Marne; Michel Vivat, Lagny-sur-Marne, both of France

[73] Assignee: Roussel Uclaf, Paris, France

[21] Appl. No.: 695,485

[22] Filed: Jan. 28, 1985

[30] Foreign Application Priority Data

Feb. 3, 1984 [FR] France .................. 84 01684

[51] Int. Cl.$^4$ ........................................... C07J 21/00
[52] U.S. Cl. ................................ 260/239.5; 260/397.3
[58] Field of Search ..................... 260/397.3, 239.5

[56] References Cited

U.S. PATENT DOCUMENTS 4,267,106  5/1981  Marx et al. .................... 260/239.5
4,328,221  5/1982  Farago et al. .................. 260/239.5

Primary Examiner—Elbert L. Roberts
Attorney, Agent, or Firm—Bierman, Peroff & Muserlian

[57] ABSTRACT

A novel process for the preparation of prednisone derivatives of the formula

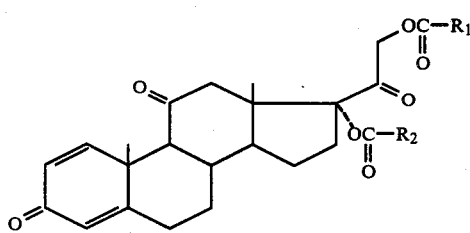

wherein $R_1$ is alkyl of 1 to 4 carbon atoms and $R_2$ is selected from the group consisting of hydrogen and hydrocarbon of 1 to 8 carbon atoms comprising reacting a compound of the formula

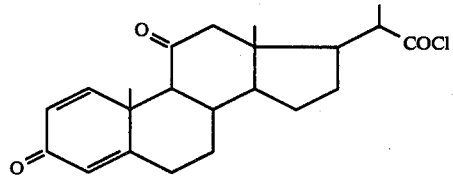

with a reducing agent to obtain a compound of the formula

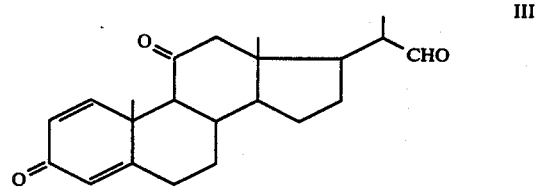

reacting the latter with a strong base in the presence of copper ions and oxygen to obtain a compound of the formula

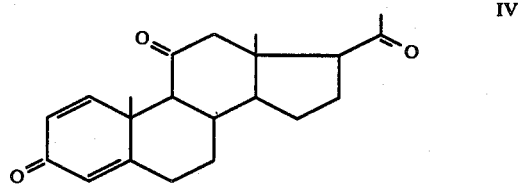

reacting the latter with hydroxylamine to obtain a compound of the formula

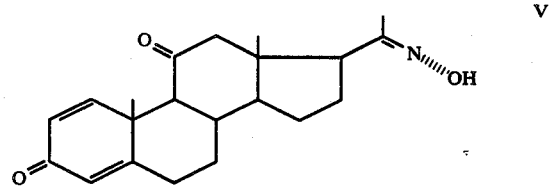

in its syn or anti isomeric form or a mixture thereof, reacting the latter with an acylating agent derived from a radical of the formula

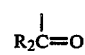

and with a reducing agent to obtain a compound of the formula

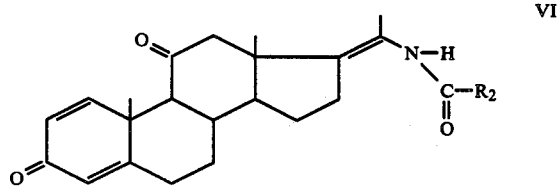

in its Z or E isomeric form or a mixture thereof, subjecting the latter to treatment with an epoxidizing agent and then a dehydrating agent to obtain a compound of the formula (Abstract continued on next page.)

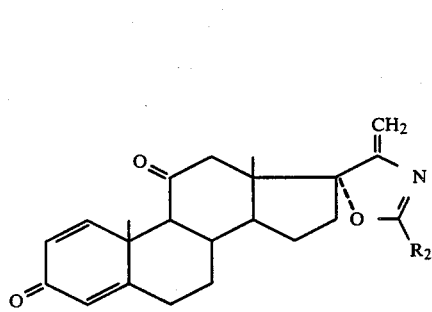
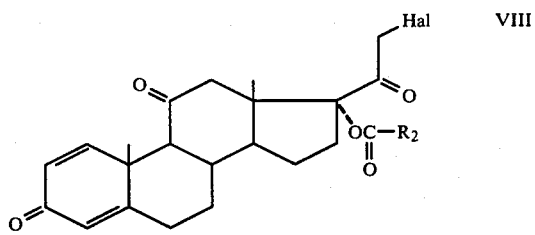
reacting the latter with a halogenation agent and subjecting the resulting product to hydrolysis to obtain a compound of the formula
wherein Hal is a halogen and reacting the latter with a derivative of an acyl of the formula $R_1CO-$ to obtain the compound of formula I which are known compounds.
10 Claims, No Drawings

PROCESS FOR THE PRODUCTION OF PREDNISONE 17.21-DIACYLATES

STATE OF THE ART

Boar et al/JCS. Perkin transactions I p. 1242-1244-/describes the reaction of lead tetraacetate with a steroid containing in the 17-position the group $$=\overset{\overset{CH_3}{|}}{C}-NH-\overset{\overset{O}{\|}}{C}-CH_3$$

Barton et al/JCS. Chem. Comm. (1981) no 15 p. 774.775/describes smooth reactions of steroidal 17-ketones with diethyl α-isocyano ethyl phosphonate to give after oxidative and hydrolytic reactions the dihydroxy acetone side-chain of corticosteroids.

In tetrahedro Letters no 12 p. 985–988 (1969) a ketone synthesis is described from copper-catalysed oxygenation of branched aldehydes.

Chemical Abstracts Vol. 97 no 21 (1982) p. 862 no 182741-a describes the preparation of Pregna 1,4-diene 3,20-dione 20-oxime by reacting the corresponding 3,20-dione with hydroxylamine.

U.S. Pat. No. 4,401,596 describes novel 17-oxazoline steroids.

OBJECTS OF THE INVENTION

It is an object of the invention to provide a novel process for the preparation of prednisone derivatives of formula I and new intermediates formed therein.

This and other objects and advantages of the invention will become obvious from the following detailed description.

THE INVENTION

The novel process of the invention for the preparation of prednisone derivatives of the formula

I wherein $R_1$ is alkyl of 1 to 4 carbon atoms and $R_2$ is selected from the group consisting of hydrogen and hydrocarbon of 1 to 8 carbon atoms comprises reacting a compound of the formula

II with a reducing agent to obtain a compound of the formula

III reacting the latter with a strong base in the presence of copper ions and oxygen to obtain a compound of the formula

IV reacting the latter with hydroxylamine to obtain a compound of the formula

V in its syn or anti isomeric form or a mixture thereof, reacting the latter with an acylating agent derived from a radical of the formula $$\overset{|}{R_2C}=O$$

and with a reducing agent to obtain a compound of the formula

VI in its Z or E isomeric form or a mixture thereof, subjecting the latter to treatment with an epoxidizing agent and then a dehydrating agent to obtain a compound of the formula

VII reacting the latter with a halogenation agent and subjecting the resulting product to hydrolysis to obtain a compound of the formula

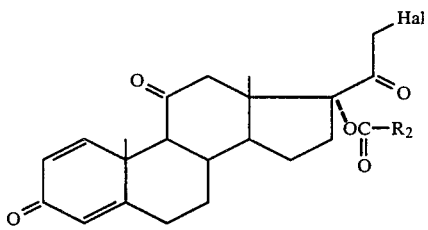

wherein Hal is a halogen and reacting the latter with a derivative of an acyl of the formula $R_1CO-$ to obtain the compound of formula I.

Examples of $R_1$ as alkyl of 1 to 4 carbon atoms and $R_2$ as hydrocarbon of 1 to 8 carbon atoms are methyl, ethyl, propyl, isopropyl, butyl and tert.-butyl.

In a preferred mode of the process of the invention, the reducing agent is selected from the group consisting of tri-tert butoxy aluminum lithium hydride, copper bis-triphenyl phosphine borohydride, tetramethyl ammonium hydriodofer tetracarbonyl, sodium borohydride in dimethylformamide, tris n-butyl tin hydride possibly catalyzed by palladium. The reduction of the product of formula II can also be carried out by the Rosenmund method.

The strong base with which the product of formula III is treated to obtain the product of formula IV is preferably potassium tert-butylate or 1,4-diazabicyclo[2,2,2]octane. The cupric ions are preferably introduced by cupric acetate and the oxygen is preferably introduced by bubbling in.

The product of formula IV is treated with hydroxylamine preferably in a slightly acidic medium such as a buffered acetic acid-sodium acetate mixture. Hydroxylamine is preferably used in the form of its hydrochloride and the reaction can be effected in a solvent or a mixture of solvents such as pyridine, methanol-dioxane, methanol or methanol-water. The reaction is preferably in a buffered acetic acid-sodium acetate-water medium. The temperature can be between ambient temperature and 100° C. and the duration of the reaction can vary for example, between 2 and 40 hours.

The conversion of the products of formula V into products of formula VI is preferably carried out by using the following reagents: the acylation reagent is a standard reagent known in organic chemistry; for example there can be used an anhydride-acid mixture of the formula $(R_2CO)_2O$ and $R_2CO_2H$; and the reducing agent is preferably a metal such as iron or nickel and the reaction temperature is between 20° and 90° C., preferably about 55°-60° C.

The conversion of products of formula VI to products of formula VII is preferably carried out with the help of an epoxidizing agent which is a peracid chosen from the m-chloroperbenzoic acid, perphthalic acid, peracetic acid and performic acid. The acid resulting from the epoxidizing reaction, name m-chlorobenzoic acid, phthalic acid, acetic acid, or formic acid, favors the dehydration reaction which is carried out by heating, for example at reflux in a solvent such as toluene or methylene chloride. The water resulting from the reaction can be eliminated by azeotropy.

The conversion of products of formula VII to products of formula VIII is carried out in the first place by the action of a halogenating reagent, preferably by bromination with the preferred reagent being pyridinium perbromide Py $H^+$, $Br_3^-$. The reaction is preferably done in the presence of a base such as pyridine or another tertiary amine.

A product is thus intermediately obtained of the formula

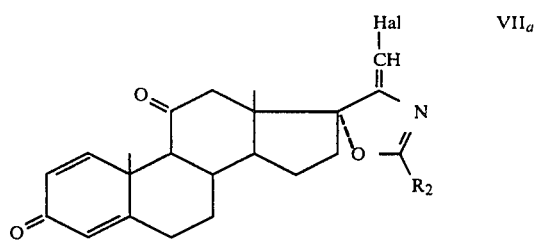

wherein Hal is halogen, preferably bromine, which can be isolated. This product is then converted into the product of formula VIII by the action of a hydrolysis agent, preferably a weak acid such as acetic acid or formic acid diluted with water. The hydrolysis reaction is preferably carried out by heating, for example at reflux.

The conversion of the products of formula VIII to products of formula I is preferably carried out with the help of a salt of the formula $R_1CO_2A$ wherein A is an alkali metal atom, preferably sodium. The reaction is preferably carried out in an aqueous acid medium, optionally in the presence of a polar solvent miscible in water such as dimethylformamide. Thus the operation can be done in an acetic acid-water-dimethylformamide medium and the reaction is preferably carried out by heating.

The process is preferably effected to obtain a compound of formula I wherein $R_1$ is methyl and $R_2$ is alkyl of 1 to 4 carbon atoms. Methyl is also the preferred value of $R_2$.

In a preferred method of the process (a) the reducing agent used to convert the products of formula II into the products of formula III is tris n-butyl tin hydride catalyzed by palladium; (b) the products of formula III are converted into products of formula IV with 1,4-diazabicyclo [2,2,2]octane in the presence of cupric acetate and with bubbling in oxygen, (c) the products of formula V are converted into products of formula VI with an acetic anhydride-acetic acid mixture in the presence of iron; (d) the products of formula VI are converted into products of formula VII with m-chloroperbenzoic acid; and (e) the halogenation agent to convert the products of formula VII into products of formula VIII is pyridinium perbromide.

Among the different stages of the process, the invention is more particularly characterized by the reaction of products of formula V to form the products of formula VI. When the acylation reaction is carried out in the presence of a reducing agent, particularly iron, the products of formula VI are obtained directly without passing intermediately by the diacylation product, the formation of which is thus prevented. Thus, a better yield is obtained of the product with formula VI. A two step process, including the intermediate formation of a diacylation product, on products of a different structure than those of the present product, is described in the Journal of the Chemical Society, Perkin Transactions I, 1975, p. 1242-1244.

Finally, the 3-keto-$\Delta^{1,4}$-structure of the products of the invention is very fragile and easily gives rise, particularly in an acid medium, to the corresponding aromatization product. Now surprisingly, such a secondary reaction is not seen; particularly, the reaction V→VI and VII→VII$_a$ which could give rise to such an aromatization are carried out in a very satisfying manner.

The new industrial products of the invention are the products of formulae III, V, VI, VII, VII$_a$ and VIII as described above. Particularly preferred intermediates are the products of formula III and formula D:

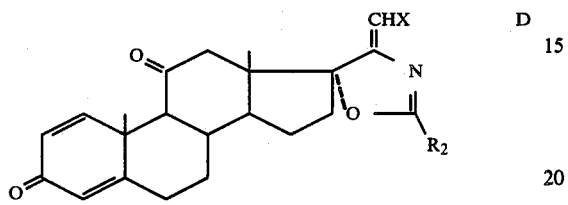

wherein $R_2$ has the above definition and X is hydrogen or halogen.

Another feature of the present invention is the preparation of the products of formula VI starting with the products of formula IV according to the scheme:

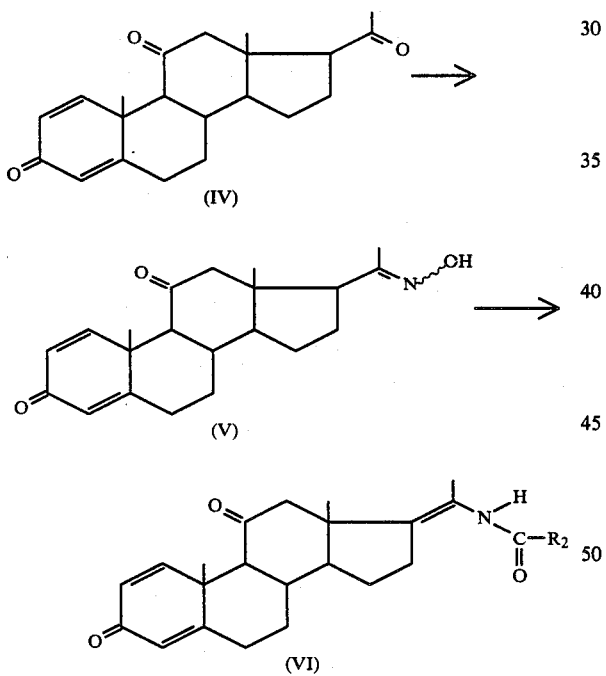

wherein $R_2$ has the above definition, and the use of the products of formula VI for the preparation of the products of formula I according to the scheme:

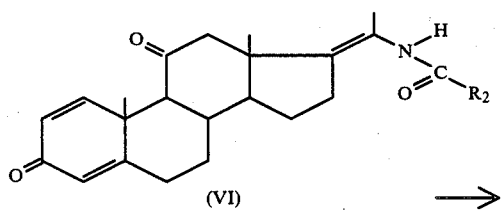

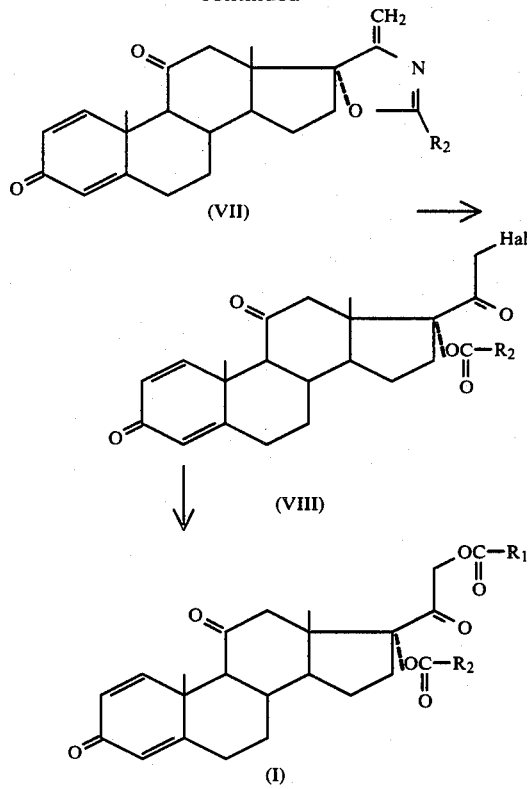

wherein $R_1$, $R_2$ and Hal have the above definitions. Naturally, each of the different stages is carried out in the conditions indicated above.

The product of formula II is described in European patents No. 39893 and No. 39895. The product of formula IV is described for example in U.S. Pat. No. 4,434,080.

The products of formula I are generally known and the product wherein $R_1=R_2=CH_3$ is, for example, described in Belgian Pat. No. 661,975. The conversion of the products of formula I to pharmacologically active products, particularly prednisone or prednisolone, is described in the literature.

In the following example, there are described several preferred embodiments to illustrate the invention. However, it should be understood that the invention is not intended to be limited to the specific embodiments.

EXAMPLE 1

17α,21-bis(acetyloxy)-$\Delta^{1,4}$-pregnadiene-3,11,20-trione

STEP A:

$\Delta^{1,4}$-pregnadiene-3,11-dione-20-carboxaldehyde

A mixture of 65 mg of palladium chloride, 480 mg of triphenylphosphine and 5 ml of dioxane was stirred under argon for 40 minutes at 25° C. and then a solution of 13.5 g of $\Delta^{1,4}$-pregnadiene-3,11-dione-20-carboxylic acid chloride in 80 ml of dioxane was added. The solution obtained was brought to a temperature of 30° C. and then over 50 minutes, a solution of 12 ml of tributyl tin hydride in 20 ml of dioxane was added. After stirring for 15 minutes more and then concentrating under reduced pressure, 27 g of $\Delta^{1,4}$-pregnadiene-3,11-dione-20-carboxaldehyde with Rf=0.3 (toluene-ethyl acetate 6:4) were obtained which was used as is in the following step.

STEP B: Δ$^{1,4}$-pregnadiene 3,11,20-trione

Over night, a mixture of 20 g of Δ$^{1,4}$-pregnadiene-3,11-dione-20-carboxaldehyde, 100 ml of dimethylformamide, 2.02 g of 1,4-diazabicyclo[2,2,2]octane, 0.16 g of hydrated copper acetate and 0.13 g of 2,2'-bipyridine was heated to 40°–45° C. while bubbling in a current of oxygen. The mixture was poured into a mixture of 1 liter of water and ice and 4 ml of 12N hydrochloric acid. After extracting three times with 400 ml of ethyl acetate, the combined organic phases were washed with water, dried and concentrated under reduced pressure to obtain 25 g of crude product which was chromatographed on silica (eluent:toluene-ethyl acetate 1-1) to obtain 7.65 g of Δ$^{1,4}$-pregnadiene 3,11,20-trione with Rf=0.2 (toluene-ethyl acetate 6-4).

STEP C: Δ$^{1,4}$-pregnadiene-3,11,20-trione-20-oxime

A mixture of 4.5 g of the product of Step B in 18 ml of acetic acid was stirred at 25° C. until completely dissolved and then 5 ml of distilled water and 4.5 g of sodium acetate were added both at once. After stirring for 10 minutes at 25° C. and then cooling to 18° C., 1.15 g of hydroxylamine hydrochloride were added all at once, and stirring was maintained at 18°–20° C. After 2 hours, the mixture was poured with stirring into 250 ml of water and ice and then left to rest for 30 minutes. After separating, washing in water and drying at reduced pressure at 40° C. for 16 hours, 4.67 g of Δ$^{1,4}$-pregnadiene-3,11,20-trione-20-oxime with Rf=0.3 (eluent:methylene chloride-acetone 8-2) were obtained.

STEP D: E and Z isomers of N-(Δ$^{1,4,17(20)}$-pregnatrien-3,11-dione-20-yl)acetamide A mixture of 2.97 g of the product of Step C, 15 ml of acetic anhydride and 10 ml of acetic acid was heated with stirring to 55° C. for 30 minutes, then 1 g of powdered iron was added over 30 minutes at 55° C. After 2 hours 15 minutes at 55° C., the mixture was cooled to +10° C. and poured with stirring into 250 ml of water and ice. After extracting with methylene chloride, washing with an aqueous solution of sodium bicarbonate, drying and concentrating under reduced pressure, 3.6 g of crude product were obtained which were chromatographed on silica (eluent:toluene-acetone 6/4 then 5/5) to obtain after drying, 2.72 g of E and Z isomers of N-(Δ$^{1,4,17(20)}$-pregnatrien-3,11-dione-20-yl)acetamide.

STEP E: (17α) 2'-methyl-4'-methylene-spiro[Δ$^{1,4}$-androstadiene 17, 5'(4'H)oxazole]-3,11-dione A mixture of 368 mg of the product of Step D in 15 ml of methylene chloride was stirred at 20° C. until completely dissolved and after cooling to 0° C., 207 mg of m-chloroperbenzoic acid were added all at once. The mixture was maintained at 0°–3° C. for 30 minutes and was heated to reflux of methylene chloride for 2 and a quarter hours. After cooling to 20° C. and washing with a 10% aqueous solution of sodium bicarbonate, then with water, drying and concentrating, the residue was chromatographed on silica (eluent:methylene-chloride acetone 85/15 then 80/20 then 60/40). After concentrating and drying under reduced pressure, 199 mg of (17α) 2'-methyl-4'-methylene-spiro[Δ$^{1,4}$-androstadiene 17, 5'(4'H)oxazole]-3,11-dione with Rf=0.4 (methylene chloride-acetone 80/20) were obtained.

STEP F: (17α)-4'-(bromomethylene)-2-methyl-spiro[-Δ$^{1,4}$-androstadiene-17,5'(4'H)oxazole]-3,11-dione A mixture of 0.89 g of the product of Step E, 34 ml of methylene chloride and 1.7 ml of pyridine was cooled to 0° C. and over 15 minutes, 0.86 g of pyridinium perbromide were added. After two hours at between 0° and 3° C., the mixture was washed with dilute aqueous solution of sodium thiosulfate, then with water, and then the methylene chloride was distilled off under reduced pressure to obtain 2 g of crude (17α)-4'-(bromomethylene)-2-methyl-spiro[-Δ$^{1,4}$-androstadiene-17,5'(4'H)oxazole]-3,11-dione with Rf=0.5 (eluent:methylene chloride-acetone 8/2) which is used as is for the following step.

STEP G: 17α-(acetyloxy)-21-bromo-Δ$^{1,4}$-pregnadiene-3,11,20-trione

A mixture of 2.5 g of the product of Step F in 10 ml of acetic acid and 10 ml of water was refluxed for 6 hours under nitrogen and it was then cooled to ambient temperature and poured into 100 ml of iced water. After extracting with methylene chloride, washing three times with a 10% aqueous solution of sodium bicarbonate, then with water, drying and concentrating to dryness under reduced pressure, 1.03 g of crude 17α-(acetyloxy)-21-bromo-Δ$^{1,4}$-pregnadiene-3,11,20-trione with Rf=0.53 (eluent:methylene chloride-acetone 8/2) were obtained which was used as is in the following step.

STEP H: 17α,21-bis(acetyloxy)-Δ$^{1,4}$-pregnadiene-3,11,20-trione

A mixture of 1.03 g of the product of Step G, 3 ml of dimethylformamide, 0.6 g of sodium acetate, 0.1 ml of acetic acid and 0.05 ml of water was heated at 60° C. under nitrogen for 19 hours and then, 0.6 g of sodium acetate, 0.1 ml of acetic acid and 2 ml of dimethylformamide were added all at once. The mixture was maintained at 60° C. for 9 hours and after cooling to ambient temperature and pouring into 100 ml of water, extracting with methylene chloride, washing with distilled water, drying and concentrating under reduced pressure, 1.05 g of 17α,21-bis(acetyloxy)-Δ$^{1,4}$-pregnadiene-3,11,20-trione were obtained which were chromatographed on silica (eluent:methylene chloride acetone 9-1).

After concentrating and drying under reduced pressure, 566 mg of defined product were obtained.

Various modifications of the process of the invention may be made without departing from the spirit or scope thereof and it should be understood that the invention is intended to be limited only as defined in the appended claims.

What we claim is:

1. A process for the preparation of prednisone derivatives of the formula wherein $R_1$ is alkyl of 1 to 4 carbon atoms and $R_2$ is selected from the group consisting of hydrogen and hydrocarbon of 1 to 8 carbon atoms comprises reacting a compound of the formula

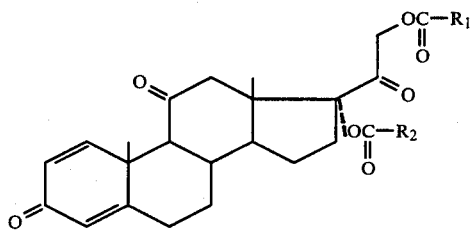  I

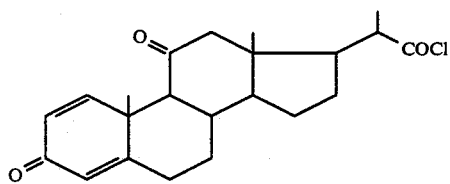  II with a reducing agent to obtain a compound of the formula

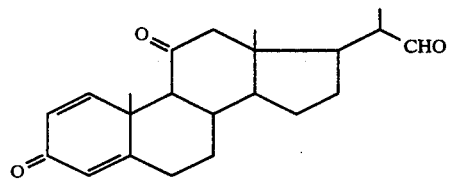  III reacting the latter with a strong base in the presence of copper ions and oxygen to obtain a compound of the formula

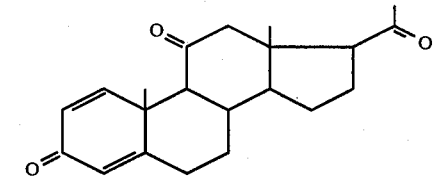  IV reacting the latter with hydroxylamine to obtain a compound of the formula

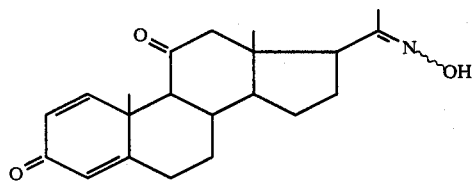  V in its syn or anti isomeric form or a mixture thereof, reacting the latter with an acylating agent derived from a radical of the formula

and with a reducing agent to obtain a compound of the formula

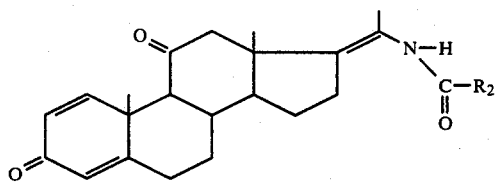  VI in its Z or E isomeric form or a mixture thereof, subjecting the latter to treatment with an epoxidizing agent and then a dehydrating agent to obtain a compound of the formula

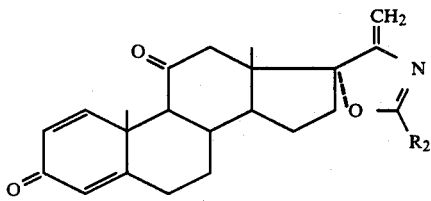  VII reacting the latter with a halogenation agent and subjecting the resulting product to hydrolysis to obtain a compound of the formula

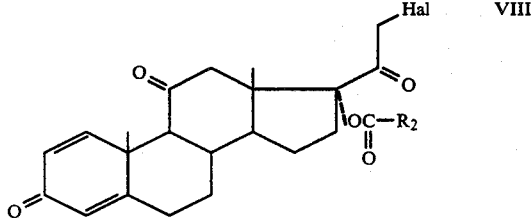  VIII wherein Hal is a halogen and reacting the latter with a derivative of an acyl of the formula $R_1CO-$ to obtain the compound of formula I.

2. The process of claim 1 wherein the reducing agent is tris n-butyl tin hydride catalyzed with palladium.

3. The process of claim 1 wherein the compound of formula III is reacted with 1,4-diazabicyclo[2,2,2]octane in the presence of cupric acetate while bubbling in oxygen.

4. The process of claim 1 wherein the compound of formula V is reacted with a mixture of acetic anhydride and acetic acid in the presence of iron.

5. The process of claim 1 wherein the compound of formula VI is reacted with m-chloroperbenzoic acid.

6. The process of claim 1 wherein the halogenating agent is pyridinium perbromide.

7. A compound having a formula selected from the group consisting of

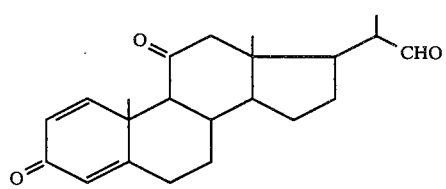
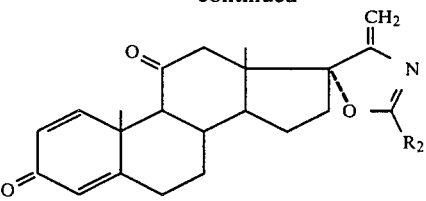
wherein $R_2$ is a hydrocarbon of 1 to 8 carbon atoms.
8. A compound of claim 7 of formula III.
9. A compound of the formula
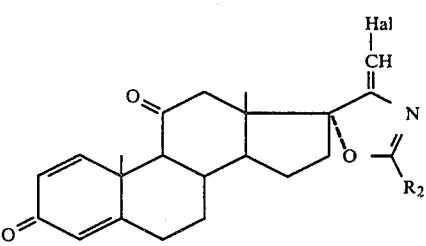
wherein $R_2$ is a hydrocarbon of 1 to 8 carbon atoms and Hal is halogen.
10. A compound of the formula
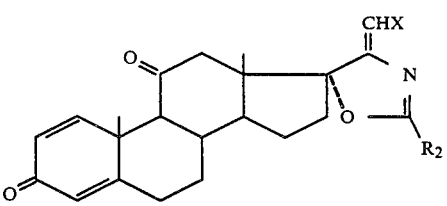
wherein $R_2$ is hydrocarbon of 1 to 8 carbon atoms and X is a halogen or hydrogen.
* * * * *